(12) United States Patent
Dollinger et al.

(10) Patent No.: US 7,750,009 B2
(45) Date of Patent: Jul. 6, 2010

(54) SUBSTITUTED PTERIDINES FOR THE TREATMENT OF INFLAMMATORY DISEASES

(75) Inventors: Horst Dollinger, Schemmerhofen (DE); Juergen Mack, Biberach (DE); Domnic Martyres, Biberach (DE); Birgit Jung, Laupheim (DE); Peter Nickolaus, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/282,548

(22) Filed: Nov. 18, 2005

(65) Prior Publication Data

US 2006/0116373 A1 Jun. 1, 2006

(30) Foreign Application Priority Data

Nov. 29, 2004 (DE) .................. 10 2004 057 595

(51) Int. Cl.
- *C07D 487/00* (2006.01)
- *C07D 491/00* (2006.01)
- *A61K 31/495* (2006.01)

(52) U.S. Cl. .................. 514/249; 544/255; 544/256; 544/257

(58) Field of Classification Search .................. 514/249; 544/255, 256, 257
See application file for complete search history.

(56) References Cited

U.S. PATENT DOCUMENTS

| | | | |
|---|---|---|---|
| 2,940,972 A | | 6/1960 | Roch |
| 4,560,685 A | * | 12/1985 | Roch et al. ............... 514/228.5 |
| 7,205,408 B2 | | 4/2007 | Davies |
| 2005/0054653 A1 | | 3/2005 | Eisenbrand et al. |
| 2006/0116371 A1 | | 6/2006 | Martyres et al. |
| 2006/0116372 A1 | | 6/2006 | Dollinger et al. |

FOREIGN PATENT DOCUMENTS

| | | | |
|---|---|---|---|
| CA | 1233179 | | 2/1988 |
| CA | 1252783 | | 4/1989 |
| CA | 1337813 | * | 12/1995 |
| DE | 3323932 A1 | | 10/1985 |
| DE | 3445298 A1 | | 6/1986 |
| DE | 3540952 A1 | | 5/1987 |
| EP | 0134922 A1 | | 3/1985 |
| EP | 0185259 A2 | | 6/1986 |
| GB | 2143232 A | | 6/1984 |
| WO | 200039129 A1 | | 7/2000 |
| WO | 2003062240 A1 | | 7/2003 |

OTHER PUBLICATIONS

Merz et al., J. Med. Chem 1998, 41, 4733-4743.*
Ambrus et al, Journal of Medicine, 1996, 27(1-2), 21-32.*
Marko et al., Biochemical Pharmacology 63 (2002) 669-676.*
Yamamoto, K. et al.; "Differential activity of drugs to induce emesis and pica behavior in Suncus murinus (house musk shrew) and rats", Physiology & Behavior, 2004, pp. 151-156, 83.
Merz K.-H. et al: "Synthesis of 7-benzylamino-6-chloro-2-piperazino-4-pyrrolidinopteridine and novel derivatives free of positional isomers. Potent inhibitors of cAMP-specific phosphodiesterase and of malignant tumor cell growth" Journal of Medicinal Chemistry, American Chemical Society, 19. Nov. 1998, pp. 4733-4743, vol. 41(24).
Doherty; Phosphodiesterase 4 inhibitors as novel anti-inflammatory agents; Current Opinion in Chemical Biology; 1999, pp. 466-473, No. 3.
Rabe et al.; Global Strategy for the Diagnosis, Management, and Prevention of Chronic Obstructive Pulmonary Disease; American Journal of Respiratory and Critical Care Medicine; vol. 176; No. 6; pp. 532-555.
Rabe et al., infra; Standards for the Diagnosis and Management of Patients with COPD; American Thoracic Society and European Respiratory Society; 2004; pp. 1-222.
Sturton et al; Phosphodiesterase 4 Inhibitors for the Treatment of COPD; Chest; 2002; 121; pp. 192S-196S.
Vignola; PDE4 Inhibitors in COPD—a more selective approach to treatment; Respiratory Medicine; 2004; vol. 98; pp. 495-503.
Press et al; PDE4 Inhibitors - A Review of the Current Field; Progress in Medicinal Chemistry; 2009; vol. 47; pp. 37-74.

\* cited by examiner

*Primary Examiner*—James O. Wilson
*Assistant Examiner*—Paul V. Ward
(74) *Attorney, Agent, or Firm*—Michael P. Morris; Mary-Ellen M. Devlin; Alan R. Stempel

(57) ABSTRACT

The invention relates to new pteridines which are suitable for the treatment of
   respiratory or gastrointestinal complaints or diseases,
   inflammatory diseases of the joints, skin or eyes,
   diseases of the peripheral or central nervous system or
   cancers, as well as pharmaceutical compositions which contain these compounds.

12 Claims, No Drawings

SUBSTITUTED PTERIDINES FOR THE TREATMENT OF INFLAMMATORY DISEASES

The invention relates to new pteridines which are suitable for the treatment of
respiratory or gastrointestinal complaints or diseases,
inflammatory diseases of the joints, skin or eyes,
diseases of the peripheral or central nervous system or cancers, as well as pharmaceutical compositions which contain these compounds.

PRIOR ART

Pteridines are known from the prior art as active substances with an antiproliferative activity. Merz et al. describe in the Journal of Medicinal Chemistry 1998, 41, 4733-4743 the preparation of 7-benzylamino-6-chloro-2-piperazino-4-pyrrolidinopteridine and derivatives thereof which are free from positional isomers. It has been shown that the compounds prepared are able to inhibit the growth of tumour cells. DE 3540952 describes 2-piperazino-pteridines which are substituted in the 6 position by a halogen atom, selected from among fluorine, chlorine or bromine. It has been shown that these compounds were able to inhibit the activity of tumour cells and human thrombocytes in vitro. DE 3323932 discloses 2-piperazino-pteridines which carry a dialkylamino, piperidino, morpholino, thiomorpholino or 1-oxidothiomorpholino group in the 4 position. It has been shown that these compounds were able to inhibit the activity of tumour cells and human thrombocytes in vitro. DE 3445298 describes pteridines with a large number of different substituents in the 2, 4, 6 and 7 position, while compounds with a 2-piperazino group on the pteridine skeleton are suitable as inhibitors of tumour growth as well as having antithrombotic and metastasis-inhibiting properties. U.S. Pat. No. 2,940,972 discloses tri- and tetrasubstituted pteridine derivatives, while general statements are made to the effect that these pteridines have valuable pharmacological properties, namely coronary-dilatory, sedative, antipyretic and analgesic effects.

The phosphodiesterase 4 inhibitors known from the prior art are known to trigger side effects such as nausea and vomiting (Doherty, 1999, Curr. Op. Chem. Biol., August 3, (4): 466-73). The substances mentioned in this invention are particularly preferably suitable for the treatment of the above-mentioned diseases, as they did not cause these side effects in an animal model for nausea and vomiting (S. Murinus, Yamamoto K. et al., Physiol. Behav., 2004, Oct. 30, 83(1), 151-6).

The aim of the present invention is to provide new compounds which are suitable for the prevention or treatment of respiratory or gastrointestinal complaints or diseases, inflammatory diseases of the joints, skin or eyes, diseases of the peripheral or central nervous system, or cancers, particularly those compounds which are characterised by reduced side effects, particularly emesis and nausea.

DESCRIPTION OF THE INVENTION

Surprisingly it has now been found that pteridines of formula 1 are suitable for the treatment of inflammatory diseases. The present invention therefore relates to compounds of formula 1

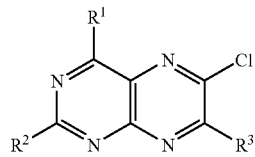

wherein $R^1$ denotes a saturated or unsaturated, five-, six- or seven-membered heterocyclic ring which may contain a nitrogen atom and another atom selected from among nitrogen, sulphur and oxygen;

$R^2$ denotes a five-, six- or seven-membered heterocyclic ring which may contain a nitrogen atom and another atom selected from among nitrogen, sulphur and oxygen;

$R^3$ is a group of formula a-i

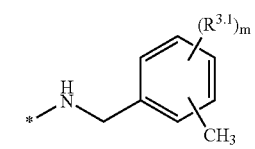
a

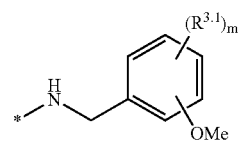
b

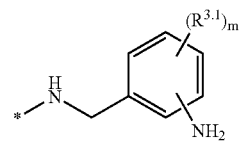
c

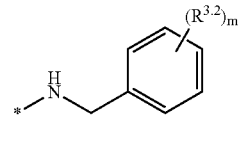
d

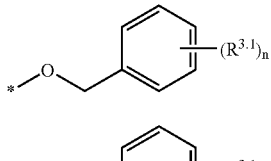
e

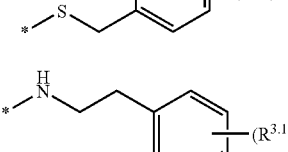
f

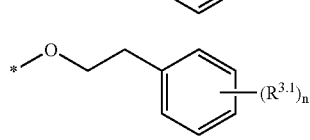
g

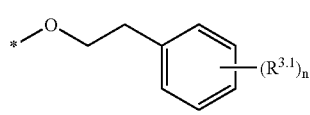
h

-continued $$*-S-CH_2CH_2-\text{C}_6H_4-(R^{3.1})_n \quad i$$

wherein
  m denotes 1, 2 or 3;
  n denotes 0, 1, 2 or 3;
  $R^{3.1}$ denotes a group selected from among $C_{1-6}$-alkyl, $C_{3-6}$-cycloalkyl, Ph, $COOR^{3.1.1}$, $CONR^{3.1.1}R^{3.1.2}$, CN, $C_{1-6}$-haloalkyl, $OR^{3.1.1}$, O—$C_{3-6}$-cycloalkyl, O—$C_{1-4}$-alkylene-$C_{3-6}$-cycloalkyl, O—$C_{1-4}$-alkylene-$CONH_2$, O—$C_{1-4}$-alkylene-$NH_2$, O—$C_{1-6}$-haloalkyl, $NR^{3.1.1}R^{3.1.2}$, $NHCOR^{3.1.1}$, $SO_2R^{3.1.1}$, $SO_2NR^{3.1.1}R^{3.1.2}$, halogen,
  $R^{3.1.1}$ denotes H, $C_{1-6}$-alkyl;
  $R^{3.1.2}$ denotes H, $C_{1-6}$-alkyl;
  $R^{3.2}$ denotes a group selected from among $C_{2-6}$-alkyl, $C_{3-6}$-cycloalkyl, Ph, $COOR^{3.2.1}$, $CONR^{3.2.1}R^{3.2.3}$, CN, $C_{1-6}$-haloalkyl, $OR^{3.2.2}$, O—$C_{3-6}$-cycloalkyl, O—$C_{1-4}$-alkylene-$C_{3-6}$-cycloalkyl, O—$C_{1-4}$-alkylene-$CONH_2$, O—$C_{1-4}$-alkylene-$NH_2$, O—$C_{1-6}$-haloalkyl, $NR^{3.2.1}R^{3.2.3}$, $NHCOR^{3.2.1}$, $SO_2R^{3.2.1}$, $SO_2NR^{3.2.1}R^{3.2.3}$, F, Br;
  $R^{3.2.1}$ denotes H, $C_{1-6}$-alkyl;
  $R^{3.2.2}$ denotes H, $C_{2-6}$-alkyl;
  $R^{3.2.3}$ denotes H, $C_{1-6}$-alkyl;

and pharmacologically acceptable salt, diastereomers, enantiomers, racemates, hydrates or solvates thereof.

Preferred compounds of formula 1 above are those wherein
$R^1$ denotes a saturated or unsaturated, five- or six-membered heterocyclic ring which may contain a nitrogen atom and another atom selected from among nitrogen and sulphur;
$R^2$ denotes a five-or six-membered heterocyclic ring which may contain one or two nitrogen atoms;

and pharmacologically acceptable salt, diastereomers, enantiomers, racemates, hydrates or solvates thereof.

Preferred compounds of formula 1 above are those wherein
$R^1$ denotes a saturated or unsaturated, five- or six-membered heterocyclic ring which may contain a nitrogen atom and optionally contains a further sulphur atom;
$R^2$ denotes a six-membered heterocyclic ring which contains two nitrogen atoms;

and pharmacologically acceptable salt, diastereomers, enantiomers, racemates, hydrates or solvates thereof.

Preferred compounds of formula 1 above are those wherein
$R^3$ is a group of formula a-i, wherein
  m denotes 1, 2 or 3;
  n denotes 0, 1, 2 or 3;
  $R^{3.1}$ denotes a group selected from among $C_{1-6}$-alkyl, $C_{3-6}$-cycloalkyl, Ph, $COOR^{3.1.1}$, $CONR^{3.1.1}R^{3.1.2}$, CN, $C_{1-6}$-haloalkyl, $OR^{3.1.1}$, O—$C_{3-6}$-cycloalkyl, O—$C_{1-4}$-alkylene-$C_{3-6}$-cycloalkyl, O—$C_{1-4}$-alkylene-$CONH_2$, O—$C_{1-4}$-alkylene-$NH_2$, O—$C_{1-6}$-haloalkyl, $NR^{3.1.1}R^{3.1.2}$, $NHCOR^{3.1.1}$, $SO_2R^{3.1.1}$, $SO_2NR^{3.1.1}R^{3.1.2}$, halogen,
  $R^{3.1.1}$ denotes H, $C_{1-6}$-alkyl;
  $R^{3.1.2}$ denotes H, $C_{1-6}$-alkyl;
  $R^{3.2}$ denotes a group selected from among $C_{2-6}$-alkyl, $C_{3-6}$-cycloalkyl, Ph, $COOR^{3.2.1}$, $CONR^{3.2.1}R^{3.2.3}$, CN, $C_{1-6}$-haloalkyl, $OR^{3.2.2}$, O—$C_{3-6}$-cycloalkyl, O—$C_{1-4}$-alkylene-$C_{3-6}$-cycloalkyl, O—$C_{1-4}$-alkylene-$CONH_2$, O—$C_{1-4}$-alkylene-$NH_2$, O—$C_{1-6}$-haloalkyl, $NR^{3.2.1}R^{3.2.3}$, $NHCOR^{3.2.1}$, $SO_2R^{3.2.1}$, $SO_2NR^{3.2.1}R^{3.2.3}$, F, Br;
  $R^{3.2.1}$ denotes H, $C_{1-6}$-alkyl;
  $R^{3.2.2}$ denotes H, $C_{2-6}$-alkyl;
  $R^{3.2.3}$ denotes H, $C_{1-6}$-alkyl;

and pharmacologically acceptable salt, diastereomers, enantiomers, racemates, hydrates or solvates thereof.

Preferred compounds of formula 1 above are those wherein
$R^3$ is a group of formula a-i, wherein
  m denotes 1, 2 or 3;
  n denotes 0, 1, 2 or 3;
  $R^{3.1}$ denotes a group selected from among $C_{1-4}$-alkyl, $C_{3-6}$-cycloalkyl, Ph, $COOR^{3.1.1}$, $CONR^{3.1.1}R^{3.1.2}$, CN, $C_{1-4}$-haloalkyl, $OR^{3.1.1}$, O—$C_{3-6}$-cycloalkyl, O—$C_{1-4}$-alkylene-$C_{3-6}$-cycloalkyl, O—$C_{1-4}$-alkylene-$CONH_2$, O—$C_{1-4}$-alkylene-$NH_2$, O—$C_{1-4}$-haloalkyl, $NR^{3.1.1}R^{3.1.2}$, $NHCOR^{3.1.1}$, $SO_2R^{3.1.1}$, $SO_2NR^{3.1.1}R^{3.1.2}$, halogen,
  $R^{3.1.1}$ denotes H, $C_{1-4}$-alkyl;
  $R^{3.1.2}$ denotes H, $C_{1-4}$-alkyl;
  $R^{3.2}$ denotes a group selected from among $C_{2-4}$-alkyl, $C_{3-6}$-cycloalkyl, Ph, $COOR^{3.2.1}$, $CONR^{3.2.1}R^{3.2.3}$, CN, $C_{1-4}$-haloalkyl, $OR^{3.2.2}$, O—$C_{3-6}$-cycloalkyl, O—$C_{1-4}$-alkylene-$C_{3-6}$-cycloalkyl, O—$C_{1-4}$-alkylene-$CONH_2$, O—$C_{1-4}$-alkylene-$NH_2$, O—$C_{1-4}$-haloalkyl, $NR^{3.2.1}R^{3.2.3}$, $NHCOR^{3.2.1}$, $SO_2R^{3.2.1}$, $SO_2NR^{3.2.1}R^{3.2.3}$, F, Br;
  $R^{3.2.1}$ denotes H, $C_{1-4}$-alkyl;
  $R^{3.2.2}$ denotes H, $C_{2-4}$-alkyl;
  $R^{3.2.3}$ denotes H, $C_{1-4}$-alkyl;

and pharmacologically acceptable salt, diastereomers, enantiomers, racemates, hydrates or solvates thereof.

Preferred compounds of formula 1 above are those wherein
$R^3$ is a group of formula a-i, wherein
  m denotes 1, 2 or 3;
  n denotes 0, 1, 2 or 3;
  $R^{3.1}$ denotes a group selected from among methyl, ethyl, propyl, OMe, OEt, OPr, F, Cl, Br, CN, $NH_2$, NHCOMe, COOH, COOMe, $CONH_2$, $SO_2Me$, $SO_2NH_2$, $SO_2NMe_2$, Ph, OH, $OCHF_2$, $OCF_3$, $CF_3$, cyclopropyl, cyclopentyl, $OCH_2CONH_2$, $OCH_2CH_2NH_2$, O-cyclopentyl, $OCH_2$-cyclopropyl;
  $R^{3.2}$ denotes a group selected from among ethyl, propyl, OEt, OPr, F, Br, CN, $NH_2$, NHCOMe, COOH, COOMe, $CONH_2$, $SO_2Me$, $SO_2NH_2$, $SO_2NMe_2$, Ph, OH, $OCHF_2$, $OCF_3$, $CF_3$, cyclopropyl, cyclopentyl, $OCH_2CONH_2$, $OCH_2CH_2NH_2$, O-cyclopentyl, $OCH_2$-cyclopropyl, and pharmacologically acceptable salt, diastereomers, enantiomers, racemates, hydrates or solvates thereof.

Preferred compounds of formula 1 above are those wherein
$R^3$ is a group of formula a-i, wherein
  m denotes 1, 2 or 3;
  n denotes 0, 1, 2 or 3;
  $R^{3.1}$ denotes a group selected from among $C_{1-4}$-alkyl, $C_{3-6}$-cycloalkyl, Ph, $CONH_2$, CN, $C_{1-4}$-haloalkyl, $OR^{3.1.1}$, O—$C_{3-6}$-cycloalkyl, $OCH_2$-cyclopropyl, O—$C_{1-4}$-alkylene-$CONH_2$, O—$C_{1-4}$-alkylene-$NH_2$, O—$C_{1-4}$-haloalkyl, $NHCOR^{3.1.1}$, $SO_2R^{3.1.1}$, $SO_2NH_2$, halogen,
  $R^{3.1.1}$ denotes H, $C_{1-4}$-alkyl;
  $R^{3.2}$ denotes a group selected from among $C_{2-4}$-alkyl, $C_{3-6}$-cycloalkyl, Ph, $CONH_2$, CN, $C_{1-4}$-haloalkyl, $OR^{3.2.1}$, O—$C_{3-6}$-cycloalkyl, $OCH_2$-cyclopropyl, O—$C_{1-4}$- alkylene-CONH$_2$, O—C$_{1-4}$-alkylene-NH$_2$, O—C$_{1-4}$-haloalkyl, NHCOR$^{3.2.2}$, SO$_2$R$^{3.2.2}$, SO$_2$NH$_2$, F, Br;

R$^{3.2.1}$ denotes H, C$_{2-4}$-alkyl;

R$^{3.2.2}$ denotes H, C$_{1-4}$-alkyl;

and pharmacologically acceptable salt, diastereomers, enantiomers, racemates, hydrates or solvates thereof.

Preferred compounds of formula 1 above are those wherein R$^3$ is a group of formula a-i, wherein m denotes 1, 2 or 3;

n denotes 0, 1, 2 or 3;

R$^{3.1}$ denotes a group selected from among methyl, isopropyl, OMe, F, Cl, CN, NHCOMe, CONH$_2$, SO$_2$Me, SO$_2$NH$_2$, Ph, OH, OCHF$_2$, OCF$_3$, CF$_3$, i-Pr, cyclopropyl, OCH$_2$CONH$_2$, OCH$_2$CH$_2$NH$_2$, O-cyclopentyl, OCH$_2$-cyclopropyl R$^{3.2}$ denotes a group selected from among CN, NHCOMe, CONH$_2$, SO$_2$Me, SO$_2$NH$_2$, Ph, OH, F, OCHF$_2$, OCF$_3$, CF$_3$, i-Pr, cyclopropyl, OCH$_2$CONH$_2$, OCH$_2$CH$_2$NH$_2$, O-cyclopentyl, OCH$_2$-cyclopropyl and pharmacologically acceptable salt, diastereomers, enantiomers, racemates, hydrates or solvates thereof.

Particularly preferred are the above compounds of formula 1, wherein

R$^1$ denotes pyrrolidine;

R$^2$ denotes piperazine;

R$^3$ denotes a group selected from among

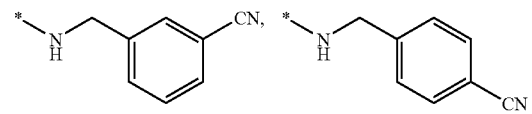

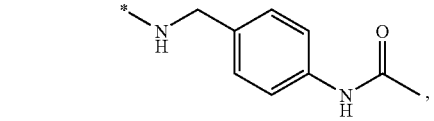

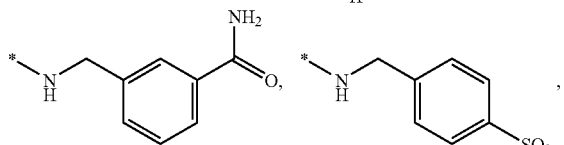

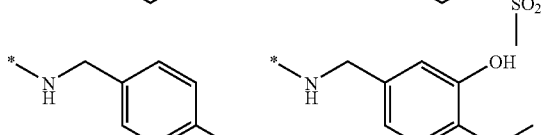

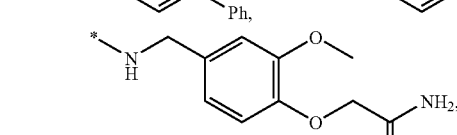

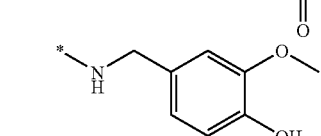

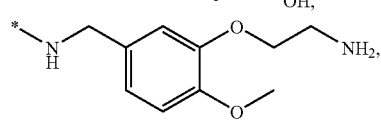

-continued

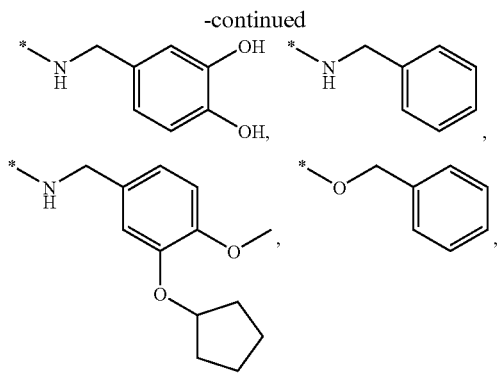

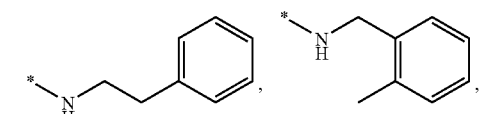

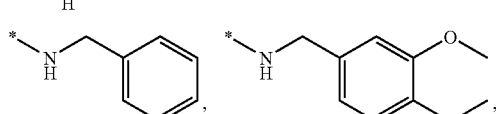

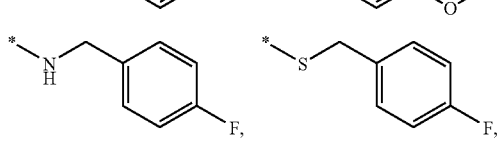

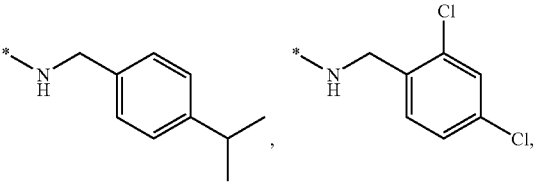

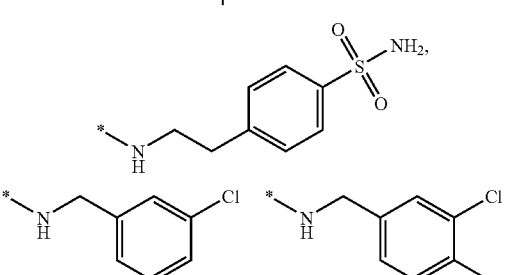

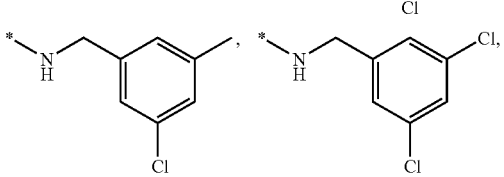

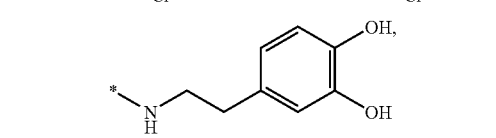

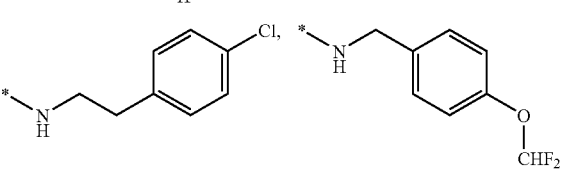

-continued

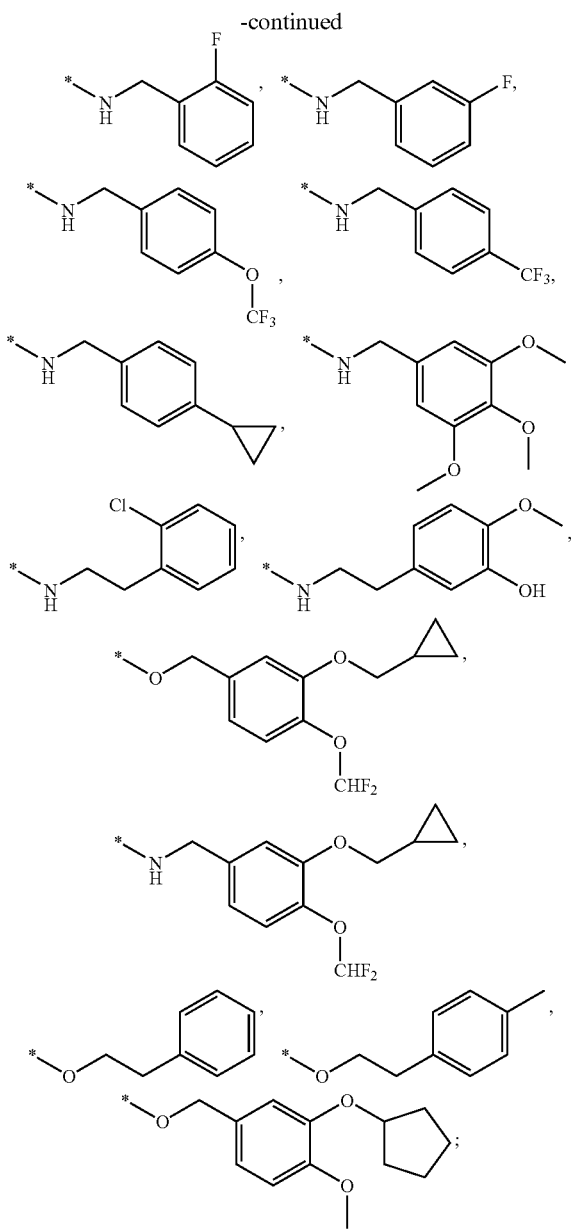

and pharmacologically acceptable salt, diastereomers, enantiomers, racemates, hydrates or solvates thereof.

TERMS AND DEFINITIONS USED

When the scope of this application, when defining possible substituents, these may also be shown in the form of a structural formula. An asterisk (*) in the structural formula of the substituent is construed as the binding site to the rest of the molecule. Thus, for example, the groups N-piperidinyl (I), 4-piperidinyl (II), 2-tolyl (III), 3-tolyl (IV) and 4-tolyl (V) are shown as follows:

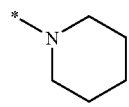

I

-continued

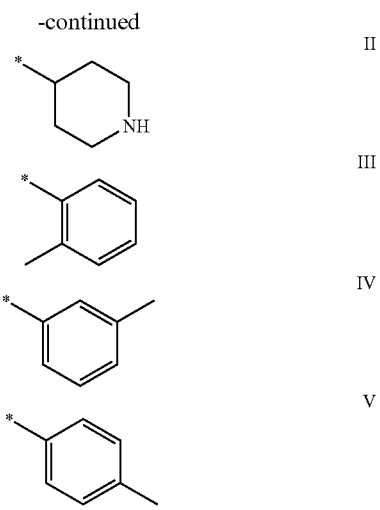

If there is no asterisk (*) in the structural formula of the substituent, each hydrogen atom may be removed from the substituent and the valency thus liberated may serve as a binding site to the rest of a molecule. Thus, for example, VI may represent 2-tolyl, 3-tolyl, 4-tolyl and benzyl.

By pharmacologically acceptable acid addition salts are meant for example those salts which are selected from among hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

By the term "$C_{1-6}$-alkyl" (including those which are part of other groups) are meant branched and unbranched alkyl groups with 1 to 6 carbon atoms, by the term "$C_{2-6}$-alkyl" are meant branched and unbranched alkyl groups with 2 to 6 carbon atoms and by the term "$C_{1-4}$-alkyl" are meant branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neopentyl or hexyl. The following abbreviations may optionally also be used for the above-mentioned groups: Me, Et, n-Pr, i-Pr, n-Bu, i-Bu, t-Bu, etc. Unless stated otherwise, the definitions propyl, butyl, pentyl and hexyl include all the possible isomeric forms of the groups in question. Thus, for example, propyl includes n-propyl and iso-propyl, butyl includes isobutyl, sec-butyl and tert-butyl etc.

By the term "$C_{1-4}$-alkylene" (including those which are part of other groups) are meant branched and unbranched alkylene groups with 1 to 4 carbon atoms. Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene. If the carbon chain is substituted by a group which together with one or two carbon atoms of the alkylene chain forms a carbocyclic ring with 3, 4, 5 or 6 carbon atoms, the following are thus included as examples of the rings:

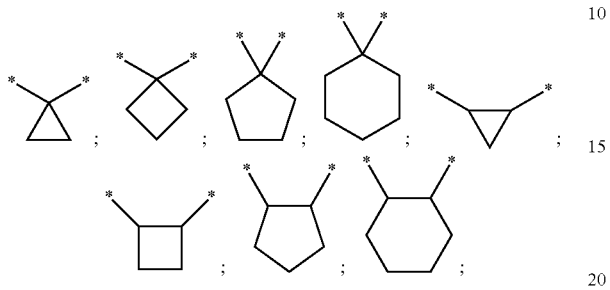

By the term "$C_{3-6}$-cycloalkyl" (including those which are part of other groups) are meant cyclic alkyl groups with 3 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

Halogen within the scope of the present invention denotes fluorine, chlorine, bromine or iodine. Unless stated to the contrary, fluorine, chlorine and bromine are regarded as preferred halogens.

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "heterocyclic rings" or "het" are meant five-, six- or seven-membered, saturated or unsaturated heterocyclic rings or 5-10 membered, bicyclic heterorings which may contain one, two or three heteroatoms, selected from among oxygen, sulphur and nitrogen, while the ring may be linked to the molecule through a carbon atom or, if available, through a nitrogen atom. The following are examples of five-, six- or seven-membered, saturated or unsaturated heterocyclic rings:

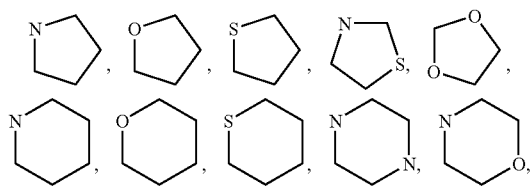

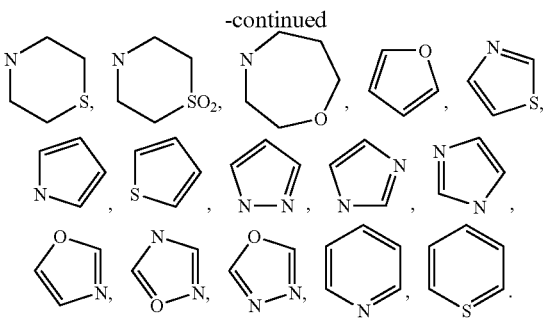

Unless otherwise mentioned, a heterocyclic ring may be provided with a keto group. Examples of this include:

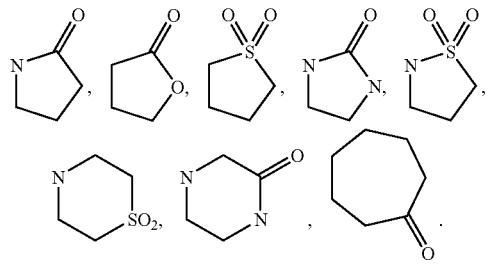

EXAMPLES

The compounds according to the invention may be prepared by methods known per se from the literature, as described for example in DE 3540952.

Example 12 a) 3-cyclopentyloxy-4-methoxy-benzaldehyde: 10.00 g (65.73 mmol) 3-hydroxy-4-methyl-benzaldehyde are dissolved in 100 ml of dimethylformamide, 11.00 ml (103.34 mmol) bromocyclopentane and 14.00 g (101.30 mmol) potassium carbonate are added. The reaction mixture is stirred for 20 hours at 100° C., then evaporated down in vacuo. The residue is extracted with ethyl acetate and water. The organic phase is dried and evaporated to dryness. Yield: 13.44 g (=93% of theoretical)

b) 3-cyclopentyloxy4-methoxy-benzaldehyde oxime: 500 mg (2.27 mmol) 3-cyclopentyloxy-4-methoxy-benzaldehyde are placed in 5 ml acetonitrile, 0.35 ml (2.53 mmol) triethylamine and 174 mg (2.50 mmol) hydroxylamine hydrochloride are added. The reaction mixture is refluxed for 24 hours with stirring, then evaporated down in vacuo. The residue is extracted with water and ethyl acetate, the combined organic phases are dried and evaporated to dryness. The product still containing contaminants is purified by chromatography. Yield: 341 mg (=64% of theoretical)

c) 3-cyclopentyloxy-4-methoxy-benzylamine: 291 mg (1.24 mmol) 3-cyclopentyloxy4-methoxy-benzaldehyde-oxime are dissolved in 3 ml of methanol, 600 mg (2.47 mmol) nickel(II)chloride hexahydrate are added and then the mixture is cooled to −50° C. 480 mg (12.44 mmol) sodium borohydride are added batchwise. The reaction mixture is stirred for 2 hours at −300 to −40° C., then slowly 12 ml of 2 N hydrochloric acid are added. The precipitate formed is suction filtered, the mother liquor is made basic with 2 N sodium hydroxide solution and extracted with ethyl acetate. The organic phase is dried and evaporated to dryness. Yield: 214 mg (=78% of theoretical)

Example 37a a) 3-cyclopropylmethoxy-4-difluoromethoxy-benzaldehyde: 4.70 g (24.98 mmol) 4-difluoromethoxy-3-hydroxy-benzaldehyde are placed in 50 ml of dimethylformamide, 4.00 g (29.63 mmol) bromomethylcyclopropane and 3.50 g (25.32 mmol) potassium carbonate are added. The reaction mixture is heated to 100° C. for 20 hours, then the dimethylformamide is concentrated by evaporation. The residue is extracted with ethyl acetate and water, the organic phase is dried and evaporated to dryness. Yield: 5.83 g (96% of theoretical)

b) (3-cyclopropylmethoxy-4-difluoromethoxy-phenyl)-methanol: 0.188 g (4.96 mmol) sodium borohydride are dissolved in 30 ml of tetrahydrofuran and 0.60 ml of methanol, and while cooling with ice a solution of 1.20 g (4.95 mmol) 3-cyclopropylmethoxy4-difluoromethoxy-benzaldehyde in 6 ml of tetrahydrofuran is added dropwise. The reaction mixture is stirred for 24 hours at ambient temperature, then evaporated down to the residue. This is combined with 80 ml 0.5 N sodium hydroxide solution and extracted with ethyl acetate. The organic phase is washed with sodium chloride solution, dried and evaporated to dryness. Yield: 0.985 g (81% of theoretical)

Example 38 a) 3-cyclopropylmethoxy4-difluoromethoxy-benzaldehyde oxime: 4.50 g (18.58 mmol) ) 3-cyclopropylmethoxy4-difluormethoxy-benzaldehyde are placed in 50 ml acetonitrile, 3.00 ml (22.00 mmol) triethylamine and 1.50 g (22.00 mmol) hydroxylamine-hydrochloride are added. The reaction mixture is refluxed for 4 hours and stirred for 16 hours at ambient temperature. Then the mixture is evaporated down to the residue. This is extracted with ethyl acetate and water, the organic phase is dried and evaporated to dryness. Yield: 4.56 g (95% of theoretical)

b) 3-cyclopropylmethoxy-4-difluoromethoxy-benzylamine: 3.50 g (13.61 mmol) of 3-cyclopropylmethoxy-4-difluoromethoxy-benzaldehyde oxime are placed in 35 ml of methanol, 3.40 g (14.02 mmol) nickel(II)chloride hexahydrate are added. The mixture is cooled to −50° C., then 5.30 g (137.30 mmol) sodium borohydride are added within 2.5 hours. The reaction mixture is stirred for 1.5 hours at −30° to −40° C., then 65 ml 16% hydrochloric acid are slowly added. The precipitate formed is suction filtered through Celite, the mother liquor is made basic. Any more precipitate obtained is in turn suction filtered and the filtrate is evaporated down in vacuo. The aqueous residue is extracted with ethyl acetate, the organic phase is dried and evaporated to dryness. Yield: 2.20 g (66% of theoretical)

Example 41 a) 3-cyclopentyloxy-4-methoxy-benzaldehyde: 2.00 g 3-hydroxy4-methyl-benzaldehyde are placed in 20 ml of dimethylformamide, 2.20 ml (20.67 mmol) bromocyclopentane and 2.80 g (20.26 mmol) potassium carbonate are added. The reaction mixture is heated to 115° C. for 3 hours, then evaporated down to the residue. This is extracted with ethyl acetate and water, the organic phase is dried and evaporated to dryness. Yield: 2.60 g (90% of theoretical)

b) (3-cyclopentyloxy4-methoxy-phenyl)-methanol: 0.50 g (13.22 mmol) sodium borohydride are dissolved in 70 ml of tetrahydrofuran and 1.40 ml of methanol, and a solution of 2.50 g (11.35 mmol) 3-cyclopentyloxy4-methoxy-benzaldehyde in 10 ml of tetrahydrofuran is added dropwise while cooling with ice. The reaction mixture is stirred for 24 hours at ambient temperature, then evaporated down to the residue. This is combined with 100 ml 0.5 N sodium hydroxide solution and extracted with ethyl acetate. The organic phase is washed with sodium chloride solution, dried and evaporated to dryness.

Yield: 2.40 g (95% of theoretical)

The following are a number of compounds, mentioned by way of example, which may be prepared analogously to one of the methods of synthesis outlined above. Melting points ($m_p$) are given in ° C.

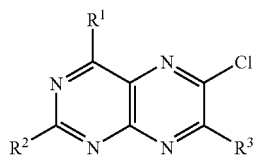

| # | $R^1$ | $R^2$ | $R^3$ | M+H or $m_p$ |
|---|---|---|---|---|
| 1. | *—N⟨pyrrolidine⟩ | *—N⟨piperazine⟩NH | *—NH—CH₂—(3-CN-phenyl) | 450/452 |
| 2. | *—N⟨pyrrolidine⟩ | *—N⟨piperazine⟩NH | *—NH—CH₂—(4-CN-phenyl) | 450/452 |

-continued

| # | R¹ | R² | R³ | M + H or m_p |
|---|----|----|----|--------------|
| 3. | *—N(pyrrolidine) | *—N(piperazine)NH | *—NH—CH2—C6H4—NHC(O)CH3 (para) | 482/484 |
| 4. | *—N(pyrrolidine) | *—N(piperazine)NH | *—NH—CH2—C6H4—C(O)NH2 (meta) | 468/470 |
| 5. | *—N(pyrrolidine) | *—N(piperazine)NH | *—NH—CH2—C6H4—SO2CH3 (para) | 503/505 |
| 6. | *—N(pyrrolidine) | *—N(piperazine)NH | *—NH—CH2—C6H4—Ph (para) | 501/503 |
| 7. | *—N(pyrrolidine) | *—N(piperazine)NH | *—NH—CH2—C6H3(OH)(OMe) | 471/473 |
| 8. | *—N(pyrrolidine) | *—N(piperazine)NH | *—NH—CH2—C6H3(OMe)(OCH2C(O)NH2) | 528/530 |
| 9. | *—N(pyrrolidine) | *—N(piperazine)NH | *—NH—CH2—C6H3(OMe)(OH) | 471/473 |
| 10. | *—N(pyrrolidine) | *—N(piperazine)NH | *—NH—CH2—C6H3(OCH2CH2NH2)(OMe) | 514/516 |
| 11. | *—N(pyrrolidine) | *—N(piperazine)NH | *—NH—CH2—C6H3(OH)(OH) | 457/459 |

-continued

| # | R¹ | R² | R³ | M + H or m_p |
|---|----|----|----|--------------|
| 12. | *—N(pyrrolidine) | *—N(piperazine)NH | *—NH—CH2—(3-O-cyclopentyl-4-methoxyphenyl) | 539/541 |
| 13. | *—N(pyrrolidine) | *—N(piperazine)NH | *—O—CH2—phenyl | 426/428 |
| 14. | *—N(pyrrolidine) | *—N(piperazine)NH | *—NH—CH2CH2—phenyl | 439/441 |
| 15. | *—N(pyrrolidine) | *—N(piperazine)NH | *—NH—CH2—(2-methylphenyl) | 439/441 |
| 16. | *—N(pyrrolidine) | *—N(piperazine)NH | *—NH—CH2—(3,4-dimethoxyphenyl) | 485/487 |
| 17. | *—N(pyrrolidine) | *—N(piperazine)NH | *—NH—CH2—(4-fluorophenyl) | 443/445 |
| 18. | *—N(pyrrolidine) | *—N(piperazine)NH | *—S—CH2—(4-fluorophenyl) | 460/462 |
| 19. | *—N(pyrrolidine) | *—N(piperazine)NH | *—NH—CH2—(4-isopropylphenyl) | 467/469 |
| 20. | *—N(pyrrolidine) | *—N(piperazine)NH | *—NH—CH2—(2,4-dichlorophenyl) | 493/495/497/499 |

-continued

| # | R¹ | R² | R³ | M + H or m_p |
|---|---|---|---|---|
| 21. | pyrrolidin-1-yl | piperazin-1-yl | *-NH-CH₂CH₂-C₆H₄-SO₂NH₂ (4-) | 518/520 |
| 22. | pyrrolidin-1-yl | piperazin-1-yl | *-NH-CH₂-C₆H₄-Cl (3-) | 459/461/463 |
| 23. | pyrrolidin-1-yl | piperazin-1-yl | *-NH-CH₂-(3,5-diCl-4-NH₂-C₆H₂) | 508/510/512/514 |
| 24. | pyrrolidin-1-yl | piperazin-1-yl | *-NH-CH₂-(3,5-diMe-C₆H₃) | 508 |
| 25. | pyrrolidin-1-yl | piperazin-1-yl | *-NH-CH₂-(3,5-diCl-C₆H₃) | 493/495/497/499 |
| 26. | pyrrolidin-1-yl | piperazin-1-yl | *-NH-CH₂CH₂-(3,4-diOH-C₆H₃) | 471/473 |
| 27. | pyrrolidin-1-yl | piperazin-1-yl | *-NH-CH₂CH₂-C₆H₄-Cl (4-) | 473/475/477 |
| 28. | pyrrolidin-1-yl | piperazin-1-yl | *-NH-CH₂-C₆H₄-OCHF₂ (4-) | 491/492 |
| 29. | pyrrolidin-1-yl | piperazin-1-yl | *-NH-CH₂-C₆H₄-F (2-) | 443/445 |

-continued

| # | R¹ | R² | R³ | M + H or m_p |
|---|----|----|----|--------------|
| 30. | *—N(pyrrolidine) | *—N(piperazine)NH | *—NH—CH₂—(3-F-phenyl) | 443/445 |
| 31. | *—N(pyrrolidine) | *—N(piperazine)NH | *—NH—CH₂—(4-OCF₃-phenyl) | 509/511 |
| 32. | *—N(pyrrolidine) | *—N(piperazine)NH | *—NH—CH₂—(4-CF₃-phenyl) | 493/495 |
| 33. | *—N(pyrrolidine) | *—N(piperazine)NH | *—NH—CH₂—(4-cyclopropyl-phenyl) | 465/467 |
| 34. | *—N(pyrrolidine) | *—N(piperazine)NH | *—NH—CH₂—(3,4,5-trimethoxy-phenyl) | 515/517 |
| 35. | *—N(pyrrolidine) | *—N(piperazine)NH | *—NH—CH₂CH₂—(2-Cl-phenyl) | 473/475/477 |
| 36. | *—N(pyrrolidine) | *—N(piperazine)NH | *—NH—CH₂CH₂—(4-OMe-3-OH-phenyl) | 485/487 |
| 37. | *—N(pyrrolidine) | *—N(piperazine)NH | *—O—CH₂—(3-OCH₂cyclopropyl-4-OCHF₂-phenyl) | 204–209° C. |

-continued

| # | R¹ | R² | R³ | M+H or m_p |
|---|----|----|----|------------|
| 38. | *—N(pyrrolidine) | *—N(piperazine)NH | *—NH-CH₂-[phenyl with O-CH₂-cyclopropyl and O-CHF₂] | 84–104° C. |
| 39. | *—N(pyrrolidine) | *—N(piperazine)NH | *—O-CH₂CH₂-phenyl | 160–161° C. |
| 40. | *—N(pyrrolidine) | *—N(piperazine)NH | *—O-CH₂CH₂-(4-methylphenyl) | 151–153° C. |
| 41. | *—N(pyrrolidine) | *—N(piperazine)NH | *—O-CH₂-[phenyl with O-cyclopentyl and O-CH₃] | 187–190° C. |

INDICATIONS

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis or interstitial pneumonia or pulmonary fibrosis of various causes, such as, for example, as a result of aspiration, inhalation of toxic gases, or bronchitis, pneumonia or interstitial pneumonia as a result of heart failure, irradiation, chemotherapy, cystic fibrosis or mucoviscidosis, or alpha 1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides interstinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

COMBINATIONS

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, dopamine agonists, H1-antihistamines, PAF-antagonists and PI3-kinase inhibitors or double or triple combinations thereof, such as for example combinations of betamimetics with corticosteroids, PDE4-inhibitors, EGFR-inhibitors or LTD4-antagonists, anticholinergics with betamimetics, corticosteroids, PDE4-inhibitors, EGFR-inhibitors or LTD4-antagonists, corticosteroids with PDE4-inhibitors, EGFR-inhibitors or LTD4-antagonists PDE4-inhibitors with EGFR-inhibitors or LTD4-antagonists EGFR-inhibitors with LTD4-antagonists.

The invention also encompasses combinations of three active substances, each selected from one of the above-mentioned categories of compounds.

FORMULATIONS

In another aspect the invention relates to medicaments for the treatment of respiratory complaints, which contain one or more of the above-mentioned pteridines of formula 1, which are used in combination with one or more additional active substances selected from among the betamimetics, anticholinergics, corticosteroids, PI3-kinase inhibitors, LTD4-antagonists, EGFR-inhibitors, dopamine agonists, H1-antihistamines or PAF-antagonists, preferably betamimetics, anticholinergics or corticosteroids, together or successively, for simultaneous, sequential or separate administration.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a pteridine and one or more combination partners selected from those described above.

What is claimed is:
1. A compound of the formula 1,

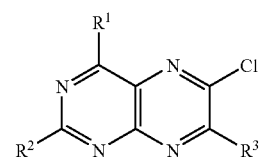

wherein
$R^1$ denotes a saturated or unsaturated, five-, six- or seven-membered heterocyclic ring which may contain a nitrogen atom and another atom selected from among nitrogen, sulphur and oxygen;
$R^2$ denotes a five-, six- or seven-membered heterocyclic ring which may contain a nitrogen atom and another atom selected from among nitrogen, sulphur and oxygen;

R³ is a group of the formula e, f, h or i:

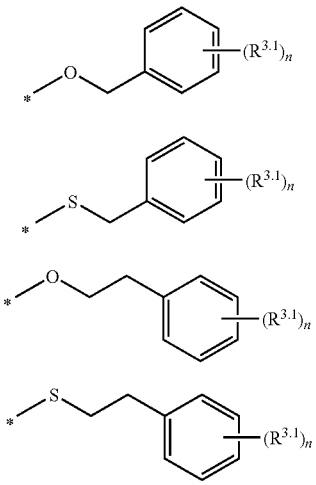

wherein
n denotes 0, 1, 2 or 3; and
R$^{3.1}$ denotes a group selected from among C$_{1-6}$-alkyl, C$_{3-6}$-cycloalkyl, aryl, COOR$^{3.1.1}$, CONR$^{3.1.1}$R$^{3.1.2}$, CN, C$_{1-6}$-haloalkyl, OR$^{3.1.1}$, O—C$_{3-6}$-cycloalkyl, O—C$_{1-4}$-alkylene-C$_{3-6}$-cycloalkyl, O—C$_{1-4}$-alkylene-CONH$_2$, O—C$_{1-4}$-alkylene-NH$_2$, O—C$_{1-6}$-haloalkyl, NR$^{3.1.1}$R$^{3.1.2}$, NHCOR$^{3.1.1}$, SO$_2$R$^{3.1.1}$, SO$_2$NR$^{3.1.1}$R$^{3.1.2}$, halogen; where
R$^{3.1.1}$ denotes H, C$_{1-6}$-alkyl; and
R$^{3.1.2}$ denotes H, C$_{1-6}$-alkyl;
or a pharmacologically acceptable salt thereof.

2. A compound of the formula 1, according to claim 1, wherein
R¹ denotes a saturated or unsaturated, five- or six-membered heterocyclic ring which may contain a nitrogen atom and another atom selected from among nitrogen and sulphur;
R² denotes a five-or six-membered heterocyclic ring which may contain one or two nitrogen atoms;
or a pharmacologically acceptable salt thereof.

3. A compound of the formula 1, according to claim 1, wherein
R¹ denotes a saturated or unsaturated, five- or six-membered heterocyclic ring which may contain a nitrogen atom and optionally contains a further sulphur atom;
R² denotes a six-membered heterocyclic ring which contains two nitrogen atoms;
or a pharmacologically acceptable salt thereof.

4. A compound of the formula 1, according to claim 1, wherein
R³ is a group of the formula e, f, h or i, wherein
n denotes 0, 1, 2 or 3; and
R$^{3.1}$ denotes a group selected from among C$_{1-6}$-alkyl, C$_{3-6}$-cycloalkyl, Ph, COOR$^{3.1.1}$, CONR$^{3.1.1}$-R$^{3.1.2}$, CN, C$_{1-6}$-haloalkyl, OR$^{3.1.1}$, O—C$_{3-6}$-cycloalkyl, O—C$_{1-4}$-alkylene-C$_{3-6}$-cycloalkyl, O—C$_{1-4}$-alkylene-CONH$_2$, O—C$_{1-4}$-alkylene-NH$_2$, O—C$_{1-6}$-haloalkyl, NR$^{3.1.1}$R$^{3.1.2}$, NHCOR$^{3.1.1}$, SO$_2$R$^{3.1.1}$, SO$_2$NR$^{3.1.1}$R$^{3.1.2}$, and halogen,
R$^{3.1.1}$ denotes H, C$_{1-6}$-alkyl; where
R$^{3.1.2}$ denotes H, C$_{1-6}$-alkyl;
or a pharmacologically acceptable salt thereof.

5. A compound of the formula 1, according to claim 1, wherein
R³ is a group of the formula e, f, h or i, wherein
n denotes 0, 1, 2 or 3; and
R$^{3.1}$ denotes a group selected from among methyl, ethyl, propyl, OMe, OEt, OPr, F, Cl, Br, CN, NH$_2$, NHCOMe, COOH, COOMe, CONH$_2$, SO$_2$Me, SO$_2$NH$_2$, SO$_2$NMe$_2$, Ph, OH, OCHF$_2$, OCF$_3$, CF$_3$, cyclopropyl, cyclopentyl, OCH$_2$CONH$_2$, OCH$_2$CH$_2$NH$_2$, O-cyclopentyl, and OCH$_2$-cyclopropyl;
or a pharmacologically acceptable salt thereof.

6. A compound of the formula 1, according to claim 1, wherein
R³ is a group of the formula e, f, h or i, wherein
n denotes 0, 1, 2 or 3; and
R$^{3.1}$ denotes a group selected from among methyl, isopropyl, OMe, F, Cl, CN, NHCOMe, CONH$_2$, SO$_2$Me, SO$_2$NH$_2$, Ph, OH, OCHF$_2$, OCF$_3$, CF$_3$, i-Pr, cyclopropyl, OCH$_2$CONH$_2$, OCH$_2$CH$_2$NH$_2$, and O-cyclopentyl,
or a pharmacologically acceptable salt thereof.

7. A compound of the formula 1 according to claim 1, wherein R¹ is pyrrolidine.

8. A compound of the formula 1 according to claim 1, wherein R² is piperazine.

9. A compound of the formula 1 according to claim 1, wherein R¹ is pyrrolidine and R² is piperazine.

10. A pharmaceutical composition comprising a compound of the formula 1, in accordance with claim 1, and a pharmaceutically acceptable carrier.

11. A method for treating COPD which comprises administering a therapeutically effective amount of a compound of the formula 1 according to claim 1.

12. A method for treating asthma which comprises administering a therapeutically effective amount of a compound of the formula 1 according to claim 1.

* * * * *